US008871986B2

(12) United States Patent
Yang et al.

(10) Patent No.: US 8,871,986 B2
(45) Date of Patent: *Oct. 28, 2014

(54) CATALYST PROMOTERS FOR PRODUCING TRIFLUOROIODOMETHANE AND PENTAFLUOROIODOETHANE

(75) Inventors: Shuwu Yang, Albany, CA (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 298 days.

This patent is subject to a terminal disclaimer.

(21) Appl. No.: 11/901,672

(22) Filed: Sep. 18, 2007

(65) Prior Publication Data

US 2008/0108854 A1    May 8, 2008

Related U.S. Application Data

(60) Provisional application No. 60/829,603, filed on Oct. 16, 2006.

(51) Int. Cl.
| | | |
|---|---|---|
| C07C 22/00 | (2006.01) | |
| C07C 25/13 | (2006.01) | |
| B01J 23/06 | (2006.01) | |
| B01J 23/10 | (2006.01) | |
| B01J 23/78 | (2006.01) | |
| C07C 17/10 | (2006.01) | |
| C07C 17/093 | (2006.01) | |
| B01J 23/04 | (2006.01) | |
| B01J 23/22 | (2006.01) | |
| B01J 23/24 | (2006.01) | |
| C07C 19/16 | (2006.01) | |
| C09K 5/04 | (2006.01) | |
| C07C 17/20 | (2006.01) | |
| C07C 17/158 | (2006.01) | |

(52) U.S. Cl.
CPC ............... *C07C 19/16* (2013.01); *B01J 23/06* (2013.01); *B01J 23/10* (2013.01); *B01J 23/78* (2013.01); *C07C 17/10* (2013.01); *C07C 17/093* (2013.01); *B01J 23/04* (2013.01); *B01J 23/22* (2013.01); *B01J 23/24* (2013.01); *C09K 5/044* (2013.01); *C07C 17/204* (2013.01); *C07C 17/158* (2013.01)
USPC ......................................................... 570/147

(58) Field of Classification Search
None
See application file for complete search history.

(56) References Cited

U.S. PATENT DOCUMENTS

| | | | | |
|---|---|---|---|---|
| 5,892,136 | A * | 4/1999 | Nagasaki et al. | 570/174 |
| 7,071,367 | B1 * | 7/2006 | Mukhopadhyay et al. | 570/101 |
| 7,132,578 | B1 * | 11/2006 | Mukhopadhyay et al. | 570/174 |
| 2006/0122440 | A1 * | 6/2006 | Mukhopadhyay et al. | 570/152 |
| 2009/0137852 | A1 * | 5/2009 | Yang et al. | 570/137 |

FOREIGN PATENT DOCUMENTS

| | | |
|---|---|---|
| FR | 2794456 | 12/2000 |
| JP | 2005-8453 | 1/2005 |
| KR | 2004043774 | 5/2004 |

OTHER PUBLICATIONS

Derwent abstract of FR2794456 published Dec. 8, 2000.*
KR-20040043774, published 2004, 14 pages.*
English translation of KR-20040043774, 2004, 17 pages.*
Nagasaki et al; "*The Development of a Novel Catalytic Technology for CF3I Manufacture*;" Halon Options Technical Working Conference; May 2000; pp. 180-185.
Noritaka Nagasaki; "*A Novel Catalytic Technology for the Manufacture of CF3I*;" Speciality Chemicals Magazine; Jun. 2002; pp. 31-32.
Nagasaki, N "A Novel Catalytic Technology for the Manufacture of CF3I", vol. 22, No. 5, 2002, pp. 31-32, XP009066299.
Lee, Kyong-Hwan, et al "Synthesis of CF3I by Direct Iodination of CH3COOH on Solid Catalyst", 2002, XP002379479.
Nagasaki, N, et al Industrial Process for the Fluorinated Organic Compounds in the Presence of Unique Solid Catalyst, XP002473916, 2002.

* cited by examiner

*Primary Examiner* — Clinton Brooks
(74) *Attorney, Agent, or Firm* — Bruce O. Bradford

(57) ABSTRACT

The present invention provides a process for the preparation of a fluoroiodoalkane compound represented by the formula $CF_3(CF_2)_n$—I, wherein n is 0 or 1. The process includes the step of contacting: (i) a compound represented by the formula $CF_3(CF_2)_n$—Y, wherein Y is selected from H, Cl, Br, and COOH and n is 0 or 1; (ii) a source of iodine; (iii) an alkali or alkaline earth metal salt catalyst supported on a carrier; and (iv) a catalyst promoter for the alkali or alkaline earth metal salt catalyst. The catalyst promoter includes at least one element selected from a transition metal element, a rare earth metal element, a main group element other than the alkali or alkaline earth metal element, any salts thereof, and any combinations thereof. The contacting is carried out at a temperature and pressure and for a length of time sufficient to produce the fluoroiodoalkane compound. The contacting may be carried out in the presence or absence of a solvent and in the presence or absence of oxygen.

52 Claims, No Drawings

CATALYST PROMOTERS FOR PRODUCING TRIFLUOROIODOMETHANE AND PENTAFLUOROIODOETHANE

CROSS-REFERENCE TO A RELATED APPLICATION

The present application claims priority from U.S. Provisional Patent Application No. 60/829,603, filed Oct. 16, 2006, the contents of which are incorporated herein by reference.

BACKGROUND OF THE INVENTION

1. Field of the Invention

The present invention generally relates to a process for the preparation of trifluoroiodomethane ($CF_3I$) by the reaction of trifluoromethane ($CF_3H$) and iodine ($I_2$) in the presence of new catalyst promoters employed in the presence or absence of oxygen. More particularly; the present invention relates to catalyst promoters for the direct synthesis of trifluoroiodomethane ($CF_3I$) from the reaction of trifluoromethane ($CF_3H$) with iodine ($I_2$) in the presence or absence of oxygen.

2. Description of the Related Art

Trifluoroiodomethane ($CF_3I$) is a potential fire extinguishing agent that can be used as a substitute for Halon 1301 ($CBrF_3$) and Halon 1211 ($CBrClF_2$), which are ozone-depleting substances. It is also a potential refrigerant with a low global warming effect.

Trifluoroiodomethane has heretofore been produced by reacting trifluoromethane ($CF_3H$) with iodine in the presence or absence of oxygen using conventional iodination catalysts. U.S. Pat. No. 5,892,136 (1999) to Nagasaki et al. and Japanese Patent No. JP 52-68110 (1977) to N. Nomura describe methods for producing trifluoroiodomethane. Japanese Patent No. JP 2005-8453 (2005) to Nagasaki et al. describes a method and apparatus for producing trifluoroiodomethane. An article by Nagasaki et al. in *Catal. Today,* 88, pages 121-126 (2004), provides a study on a novel catalytic reaction and its mechanism for $CF_3I$ synthesis. Another article by Nagasaki et al. in *Proceedings of the Halon Options Technical Working Conference*, Albuquerque, N. Mex., 2000, pp. 180-185 provides a description of the development of a novel catalytic technology for $CF_3I$ manufacture. Still another article by N. Nagasaki in *Specialty Chemicals Magazine*, June 2002, pp. 31-32 provides a description of a novel catalytic technology for the manufacture of $CF_3I$. French Patent No. FR 2,794,456 (2000) to Jean Marc Sage describes a process for producing trifluoroiodomethane, pentafluoroiodoethane (i.e., pentafluoromethyl iodide) or a mixture thereof.

It would be desirable to have an improved process for the preparation of $CF_3I$ by the reaction of trifluoromethane and iodine.

SUMMARY OF THE INVENTION

The present invention provides a process for the preparation of a fluoroiodoalkane compound represented by the formula:

wherein n is 0 or 1.
The process includes the step of contacting:
(i) a compound represented by the formula:

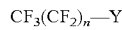

wherein Y is selected from H, Cl, Br, and COOH;
wherein n is 0 or 1;
(ii) a source of iodine;
(iii) an alkali or alkaline earth metal salt catalyst supported on a carrier; and
(iv) a catalyst promoter for the alkali or alkaline earth metal salt catalyst;
wherein the catalyst promoter includes at least one element selected from a transition metal element, a rare earth metal element, a main group element other than the alkali or alkaline earth metal element, any salts thereof, and any combinations thereof;
wherein the contacting is carried out in the presence or absence of a solvent, in the presence or absence of oxygen (absence meaning substantially free of oxygen), and at a temperature and pressure and for a length of time sufficient to produce the fluoroiodoalkane compound.

Catalyst performance and reaction rates are significantly improved by employing catalyst promoters according to the present invention. When lanthanum is used as a promoter, the catalyst was found to be about 2 to 3 times as active as a corresponding lanthanum-free catalyst.

These and other benefits and advantages of the present process will become more evident from the detailed description of the preferred embodiments that follows.

DETAILED DESCRIPTION OF PREFERRED EMBODIMENTS

Conventional catalysts used in the prior art include alkali and/or alkaline earth metal salts supported on a carbonaceous carrier, which generally have low activity, low $CF_3I$ yield and short lifetime.

The process of the present invention employs novel catalyst promoters to promote catalyst activity and stability. The promoters include transition metals such as Sc, V, Cr, Fe, Co, Ni, Cu, Zn, Y, Mo, rare earth metals such as La and Ce, and some main group elements, such as B, Al, Ga, Ge, Sn, Sb, Bi.

In general, the catalyst performance is significantly improved by employing the above promoters. La, Sm, Ce and V showed the most significant effect. For example, when lanthanum was used as a promoter, the catalyst was about 2-3 times as active as a lanthanum-free catalyst.

Accordingly, the present invention provides new catalyst promoters that are useful in the direct synthesis of $CF_3I$ by reacting $CF_3H$ and $I_2$ in the presence or absence of oxygen.

$CF_3I$ is produced by a catalytic one-step process by the reaction of one or more of the following starting materials ($CF_3H$, $CF_3CF_2H$, $CF_3COOH$, $CF_3Cl$ and $CF_3Br$) with a source of iodine ($I_2$, HI, ICl or $IF_5$) in the presence or absence of a source of oxygen. In a preferred reaction, $CF_3H$ is reacted with $I_2$ in the presence of oxygen or air.

Alkaline metals (and salts thereof) useful as catalysts in the present invention include Li, Na, K, Rb, Cs, Fr, and a combination thereof. The salts include, but not limited to, nitrate, halide (fluoride, chloride, bromide and iodide), sulfate, and phosphate. The most preferred alkaline metal is K, and the preferred salt is nitrate ($—NO_3^-$) and phosphate ($—PO_4^{3-}$). Useful alkaline earth metals (and salts thereof useful as catalysts in the present invention include Be, Mg, Ca, Sr, Ba, Ra, and a combination thereof. The most preferred alkaline earth metal is Mg, and preferred salt is nitrate ($—NO_3^-$).

The catalyst system can be prepared by supporting one or more alkali and/or alkaline earth metal salts, preferably potassium salt, on a carbonaceous carrier, preferably activated carbon. Catalyst promoter(s) are supported on the carbonaceous carrier at the same time when the alkali and/or alkaline earth metal salts are impregnated. Alternatively, the catalyst system can be prepared by a stepwise impregnation method, either before or after adding the alkali or alkaline earth metal salts to the support. If desired, non-carbonaceous carriers can be employed.

The following three kinds of promoters can be used in the catalyst system according to the present invention:

(1) transition metals (and salts thereof; preferred transition metal elements include, but are not limited to, Sc, Ti, V, Cr, Mn, Fe, Co, Ni, Cu, Zn, Y, Zr, Nb, Mo, Ag, Cd, Ta, W, Au, and Hg; of these transition metals, V, Cr, Mn, Co, Ni, Zn, Y, Nb, Mo, W are more preferred; V is the most preferred transition metal and nitrate is the most preferred salt;

(2) rare earth metals (and salts thereof; preferred rare earth metal promoters include, but are not limited to, La, Ce, Pr and Sm; La is the most preferred rare earth metal and its nitrate form is the most preferred salt; and (3) main group elements (and salts thereof excluding alkali and alkaline earth metals; preferred main group elements include, but are not limited to, B, Al, Ga, Ge, Sn, Sb, and Bi; more preferred main group elements include Al, Sn and Sb; Al is the most preferred main group element and its nitrate form is the most preferred.

The promoter can be a single element in any of its naturally occurring forms, such as, metal, oxide, fluoride, chloride, bromide, iodide, nitride, sulfate, phosphate and carbide, or in a combination of any of its naturally occurring forms with a transition metal, rare earth metal, and a main group element. The nitride salt of these elements is most preferred.

The amount of a promoter suitable for use ranges from 0.01% to 50% by weight of the entire catalyst weight.

The as-prepared promoted catalysts are preferably calcined in an inert gas such as nitrogen at 150-750° C., more preferably at 300-600° C., and most preferably at 400-550° C.

Before reaction, the catalysts can also preferably be further treated in nitrogen, hydrogen, HF, $CF_3H$, $I_2$, air, oxygen, or a mixture thereof, at or below the particular reaction temperature in which it will be used. Nitrogen is a preferred.

Preferably, the reaction temperature ranges from about 150° C. to about 750° C. More preferably, the reaction temperature ranges from about 300° C. to about 600° C. Still more preferably, the reaction temperature ranges from about 400° C. to about 550° C. Most preferably, the reaction temperature ranges from about 400° C. to about 500° C.

Preferably, the reaction pressure is from about 0.001 atm to about 100 atm. More preferably, the reaction pressure ranges from about 0.1 atm to about 10 atm. Still more preferably, the reaction pressure ranges from about 0.5 atm to about 10 atm. Most preferably, the reaction pressure ranges from about 0.5 atm to about 5 atm.

Preferably, the contact time is from about 0.01 sec to about 300 hours. More preferably, the contact time is from about 0.01 sec to about 100 hours. Still more preferably, the contact time is from about 0.5 sec to about 10 hours. Still yet more preferably, the contact time is from about 1 sec to about 1 hour. Most preferably, the contact time is from about 1 sec to about 10 minutes.

In the practice of the process of the present invention, the step of contacting is most preferably carried out at a temperature from about 300° C. to about 600° C., at a pressure from about 0.1 atm to about 10 atm, and for a length of time from about 0.5 sec to about 10 hours.

The process can be either a batch process or it can be a continuous process. A continuous process is preferred. Useful reactors include fix-bed reactors and moving-bed reactors.

The reactor can further include, i.e., the process can further employ, a diluent, such as a gas and/or a solvent or mixture of solvents. Examples of useful solvents include water and ethanol. Examples of useful gases include nitrogen, helium, argon and mixtures thereof.

The process can optionally further include one or more of the following steps: (a) passing the trifluoromethyl iodide or pentafluoroethyl iodide through a scrubber containing an aqueous alkali solution; (b) passing the trifluoromethyl iodide or pentafluoroethyl iodide through a scrubber containing a drying agent; (c) cooling at a temperature below the boiling temperature of the trifluoromethyl iodide or pentafluoroethyl iodide to condense; and (d) isolating the trifluoromethyl iodide or pentafluoroethyl iodide from the reaction mixture in substantially pure form.

In operation, preferably at least 10 wt % of the reactants are converted. More preferably, at least 20 wt % of the reactants are converted, still more preferably, at least 30 wt % of the reactants, and more preferably at least about 40 wt % of the reactants are converted to products and by-products. Desirable ranges of conversion include about 30 to about 80 wt % and about 40 to about 70 wt %.

In operation, preferably at least 10 wt % of the reactants are converted to the trifluoroiodomethane, which is the selectivity of the reaction to make $CF_3I$. More preferably, at least 20 wt % of the reactants are converted to the trifluoroiodomethane, and most preferably, at least 50 wt % of the reactants are converted to the trifluoroiodomethane.

The following non-limiting examples are illustrative of the various embodiments of the present invention. It is within the ability of a person of ordinary skill in the art to select other variables from amongst the many known in the art without departing from the scope of the present invention. Accordingly, these examples shall serve to further illustrate the present invention, not to limit them.

Unless otherwise indicated, all parts and percentages related to the catalyst are on a weight basis, while all percentages related to activity, selectivity and yield are on molar basis.

Example 1

Catalyst Preparation

Preparation of K/C Catalysts (Potassium Compounds Supported on carbon): Designated amount of $KNO_3$ was dissolved in deionized water (the amount of water was calculated from the pore volume of a support). After $KNO_3$ was dissolved completely, designated amount of activated carbon (pre-dried at 100 to 120° C. for 12 hr) was slowly poured into the solution, or vice versa. The paste was stirred continuously to achieve homogeneous impregnation and then was put it in the hood overnight to allow adequate impregnation. Subsequently the impregnated sample was dried in an oven at 100 to 120° C. for 12 hr and calcined at 450 to 550° C. for 4 hr under a stream of nitrogen.

Preparation of promoted K/C catalysts: Designated amount of $KNO_3$ and designated amount of precursor of a promoter were dissolved in desired amount of deionized water. After all salts were dissolved completely, designated amount of activated carbon (pre-dried at 100-120° C. for 12 hr) was slowly poured into the solution, or vice versa. The paste was stirred continuously to achieve homogeneous impregnation and then was put it in the hood overnight to allow adequate impregnation. Subsequently, the impregnated sample was dried in an oven at about 100-120° C. for 12 hr and thereafter it was calcined at 450-550° C. for 4 hr under a stream of nitrogen.

In the stepwise impregnation method, a salt of a promoter was first impregnated on activated carbon overnight, after drying/calcination, $KNO_3$ was subsequently impregnated on activated carbon, followed by drying and calcination.

The activated carbon support used in this invention was pelletized Shirasagi C2X 4/6-2 from Japan EnviroChemicals, Ltd., which is a highly purified activated carbon support with a surface area above 1000 m$^2$/g and an average pore diameter 23 Å.

Example 2

Reactivity of K/C Catalysts Promoted by Transition Metals

The promotional effect of transition metals was investigated and some examples were listed in Table 1. For unpromoted K/C catalyst, it showed 21.5% $CF_3H$ conversion and 57.7% $CF_3I$ selectivity at 500° C., $I_2/CF_3H$ (molar ratio) =0.33, $O_2/CF_3H$ (molar ratio)=0.1, and at a contact time 20 s. When transition metals were added to K/C catalyst, significant promotional effect was observed for most of the promoters. As shown in Table 1, there were little changes in activity and selectivity when Zn and Fe were used. However, $CF_3H$ conversion was increased to 30-40% when Cu, Mo, Ni, Cr, and Co were added separately to the K/C catalyst. When 5% $V_2O_5$ was added to the K/C, the catalyst showed 47.1% $CF_3H$ conversion and 60.1% $CF_3I$ selectivity.

TABLE 1

(Effect of transition metal promoters on the reactivity of K/C. Reaction conditions: 500° C., $I_2/CF_3H$ = 0.33 (molar ratio), $O_2/CF_3H$ = 0.1 (molar ratio), contact time: 20 seconds (s); reaction time: 8 hr)

| Catalyst | $CF_3H$ conversion (%) | $CF_3I$ selectivity (%) | $CF_3I$ yield (%) |
|---|---|---|---|
| 7.5% K/C | 21.5 | 57.7 | 12.4 |
| 7.5% K-5% $Fe_2O_3$/C | 21.5 | 63.8 | 13.7 |
| 7.5% K-5% ZnO/C | 25.3 | 62.6 | 15.8 |
| 7.5% K-5% CuI/C | 29.2 | 62.2 | 18.2 |
| 7.5% K-5% $MoO_3$/C | 31.3 | 61.9 | 19.4 |
| 7.5% K-5% NiO/C | 31.9 | 52.8 | 16.9 |
| 7.5% K-5% $Cr_2O_3$/C | 35.0 | 48.7 | 17.0 |
| 7.5% K-5% CoO/C | 41.0 | 61.3 | 25.1 |
| 7.5% K-5% $V_2O_5$/C | 47.1 | 60.1 | 28.3 |

Example 3

Reactivity of K/C Catalysts Promoted by Rare Earth Metals

Table 2 shows the promotional effect of some rare earth metals. The $CF_3H$ conversion was 43.6% and $CF_3I$ selectivity was 61.1% for 7.5% K-5% $CeO_2$/C. Lanthanum showed the most significant effect compare with cerium and transition metals. The 7.5% K-5% $La_2O_3$/C catalyst had 55.6% $CF_3H$ conversion and 58.4% $CF_3I$ selectivity, which was 2 to 3 times as active as the unpromoted K/C catalyst. 7.5% K-5% $Sm_2O_3$/C exhibited similar activity and selectivity as lanthanum-promoted K/C. Lanthanum is also a good promoter for Rb/C and Cs/C. Both Rb—$La_2O_3$/C and Cs/$La_2O_3$/C gave identical activity as K—$La_2O_3$/C, but their $CF_3I$ selectivity was low (~45%). More $CF_4$ was formed on Rb—$La_2O_3$/C and Cs/$La_2O_3$/C than on K—$La_2O_3$/C.

TABLE 2

(Effect of rare earth metal promoters on the reactivity of K/C. Reaction conditions: 500° C., $I_2/CF_3H$ = 0.33 (molar ratio), $O_2/CF_3H$ = 0.1 (molar ratio), contact time: 20 s, reaction time: 8 hr)

| Catalyst | $CF_3H$ conversion (%) | $CF_3I$ selectivity (%) | $CF_3I$ yield (%) |
|---|---|---|---|
| 7.5% K-5% $CeO_2$/C | 43.6 | 61.1 | 26.6 |
| 7.5% K-5% $La_2O_3$/C | 55.6 | 58.4 | 32.5 |
| 7.5% K-5% $Sm_2O_3$/C | 54.0 | 57.9 | 31.3 |
| 7.5% Rb-5% $La_2O_3$/C | 57.0 | 45.4 | 25.9 |
| 7.5% Cs-5% $La_2O_3$/C | 54.6 | 44.6 | 24.4 |

Example 4

Effect of $La_2O_3$ Loading on the Reactivity of K—$La_2O_3$/C

As lanthanum showed the best promotional effect, the effect of $La_2O_3$ loading was investigated. As listed in Table 3, when 1% $La_2O_3$ was added, the catalyst exhibited 44.7% $CF_3H$ conversion. Therefore, only small amount of $La_2O_3$ was enough to improve catalyst activity significantly. With increasing $La_2O_3$ loading to 5%, the catalyst activity increased to ~55%. No much change in activity was found with further increasing $La_2O_3$ loading (up to 20%). Therefore, the optimized $La_2O_3$ loading is ~5%. Too high $La_2O_3$ loading resulted in the combustion of $CF_3H$ into $CO_2$ and $CF_4$ and created too many hot spots.

TABLE 3

(Effect of $La_2O_3$ loading on the reactivity of 7.5 wt. % K—$La_2O_3$/C; reaction conditions: 500° C., $I_2/CF_3H$ = 0.33 (molar ratio), $O_2/CF_3H$ = 0.1 (molar ratio), contact time: 20 s; reaction time: 8 hr)

| $La_2O_3$ loading (wt. %) | $CF_3H$ conversion (%) | $CF_3I$ selectivity (%) | $CF_3I$ yield (%) |
|---|---|---|---|
| 0 | 21.5 | 57.7 | 12.4 |
| 1.0 | 44.7 | 59.9 | 26.8 |
| 2.0 | 49.4 | 59.8 | 29.6 |
| 3.0 | 50.5 | 59.8 | 30.2 |
| 5.0 | 55.6 | 58.4 | 32.5 |
| 10.0 | 56.8 | 57.6 | 32.7 |
| 20.0 | 58.8 | 57.5 | 33.8 |

Example 5

Effect of $CeO_2$ Loading on the Reactivity of K—$CeO_2$/C

Table 4 showed the effect of $CeO_2$ loading on the reactivity of K—$CeO_2$/C catalysts. The activity of K—$CeO_2$/C catalysts continuously increased with increasing $CeO_2$ loading (from 0 to 10%). For K-10% $CeO_2$/C, it showed 52.5% $CF_3H$ conversion, which was still lower than K-5% $La_2O_3$/C, suggesting that higher $CeO_2$ loading was needed in order to get similar catalyst performance as that of K—$La_2O_3$/C.

TABLE 4

(Effect of CeO$_2$ loading on the reactivity of 7.5 wt. % K—CeO$_2$/C: reaction condition: 500° C., I$_2$/CF$_3$H = 0.33 (molar ratio), O$_2$/CF$_3$H = 0.1 (molar ratio), contact time: 20 s; reaction time: 8 hr)

| CeO$_2$ loading (wt. %) | CF$_3$H conversion (%) | CF$_3$I selectivity (%) | CF$_3$I yield (%) |
|---|---|---|---|
| 0 | 21.5 | 57.7 | 12.4 |
| 1.0 | 37.9 | 61.4 | 23.3 |
| 5.0 | 43.6 | 61.1 | 26.6 |
| 10.0 | 52.5 | 58.9 | 30.9 |

Example 6

Reactivity of K—La$_2$O$_3$/C in the Absence of Oxygen

TABLE 5

(Reactivity of K—La$_2$O$_3$/C in the absence of oxygen; reaction condition: 500° C., I$_2$/CF$_3$H = 0.33 (molar ratio), O$_2$/CF$_3$H = 0 (molar ratio), contact time: 22 s; reaction time: 8 hr)

| Catalyst | CF$_3$H conversion (%) | CF$_3$I selectivity (%) | CF$_3$I yield (%) |
|---|---|---|---|
| 7.5% K-5% La$_2$O$_3$/C | 45.8 | 71.2 | 32.6 |
| 7.5% K-15% La$_2$O$_3$/C | 42.7 | 64.3 | 27.5 |

The reactivity of lanthanum promoted catalyst was studied in the absence of oxygen. As listed in Table 5, 7.5% K-5% La$_2$O$_3$/C gave 45.8% CF$_3$H conversion and 71.2% CF$_3$I selectivity, and 7.5% K-15% La$_2$O$_3$/C exhibited 42.7% CF$_3$H conversion and 64.3% CF$_3$I selectivity even in the absence of oxygen, which were still higher than the unpromoted K/C catalyst. But in the absence of oxygen, the catalyst deactivated rapidly.

Example 7

Reactivity of K/C Promoted by Main Group Elements

The effect of main group elements was also investigated and the reactivity of K—Al$_2$O$_3$/C was given in Table 6. It can be seen that the catalyst showed a little higher activity than K/C in the presence of 1% Al$_2$O$_3$ and 2% Al$_2$O$_3$, while it totally lost activity when 5% Al$_2$O$_3$ was added to K/C.

These results indicated that some main group metals, such as, aluminum, can have promotional effect when used at certain levels of loading.

TABLE 6

(Reactivity of 7.5 wt. % K—Al$_2$O$_3$/C; reaction condition: 500° C., I$_2$/CF$_3$H = 0.33 (molar ratio), O$_2$/CF$_3$H = 0.1 (molar ratio); contact time: 20 s; reaction time: 8 hr)

| Catalyst | CF$_3$H Conversion (%) | CF$_3$I Selectivity (%) | CF$_3$I yield (%) |
|---|---|---|---|
| 7.5% K-1% Al$_2$O$_3$/C | 26.5 | 63.2 | 16.7 |
| 7.5% K-2% Al$_2$O$_3$/C | 31.5 | 65.3 | 20.6 |
| 7.5% K-5% Al$_2$O$_3$/C | 0.37 | 58.3 | 0.21 |

The present invention has been described with particular reference to the preferred embodiments. It should be understood that variations and modifications thereof can be devised by those skilled in the art without departing from the spirit and scope of the present invention. Accordingly, the present invention embraces all such alternatives, modifications and variations that fall within the scope of the appended claims.

What is claimed is:

1. A process for the preparation of a fluoroiodoalkane compound represented by the formula:

$$CF_3(CF_2)_n\text{—I}$$

wherein n is 0 or 1;
the process comprising contacting:
  (i) a compound represented by the formula:

$$CF_3(CF_2)_n\text{—Y}$$

wherein Y is selected from the group consisting of: H, Cl, and Br;
  wherein n is 0 or 1;
  (ii) a source of iodine;
  (iii) an alkali metal salt catalyst selected from the group consisting of K, Rb and Cs, and
  (iv) a catalyst promoter in the range of from 0.01 to 50% by weight of the entire catalyst weight,
at a temperature for a length of time sufficient to produce the fluoroiodoalkane compound; and
wherein the catalyst promoter comprises V$_2$O$_5$.

2. The process of claim 1, wherein the reaction is carried out in the presence of oxygen.

3. The process of claim 1, wherein the reaction is carried out in the absence of oxygen.

4. The process of claim 1, wherein the catalyst carrier is carbonaceous.

5. The process of claim 1, wherein the catalyst carrier is non-carbonaceous.

6. The process of claim 1, wherein the source of iodine is a compound selected from the group consisting of I$_2$, HI, ICl, IF$_5$, and any combination thereof.

7. The process of claim 6, wherein the source of iodine is I$_2$.

8. The process of claim 1, wherein the step of contacting is carried out at a temperature from about 300° C. to about 600° C.

9. The process of claim 8, wherein the step of contacting is carried out at a temperature from about 400° C. to about 550° C.

10. The process of claim 1, wherein the step of contacting is carried out at a pressure from about 0.1 atm to about 100 atm.

11. The process of claim 10, wherein the step of contacting is carried out at a pressure from about 0.5 atm to about 5 atm.

12. The process of claim 1, wherein the step of contacting is carried out for a length of time from about 0.01 seconds to about 300 hours.

13. The process of claim 12, wherein the step of contacting is carried out for a length of time from about 0.05 seconds to about 10 hours.

14. The process of claim 12, wherein the step of contacting is carried out for a length of time from about 1 second to about 10 minutes.

15. The process of claim 1, wherein the process is a batch process.

16. The process of claim 1, wherein the process is a continuous process.

17. The process of claim 1, wherein the contacting is carried out in a fixed-bed reactor.

18. The process of claim 1, wherein the contacting is carried out in a moving-bed reactor.

19. The process of claim 1, further comprising a diluent selected from the group consisting of a gas, a solvent, and a combination thereof.

20. The process of claim 19, wherein the diluent is a gas selected from the group consisting of nitrogen, helium, argon and any combination thereof.

21. The process of claim 19, wherein the diluent is a solvent of a liquid or gaseous fluorocarbon.

22. The process of claim 1, further comprising at least one step selected from the group consisting of the following:
   a) passing the trifluoromethyl iodide through a scrubber containing an aqueous alkali solution;
   b) passing the trifluoromethyl iodide through a scrubber containing a drying agent;
   c) cooling at a temperature below the boiling temperature of the trifluoromethyl iodide to condense; and
   d) isolating the trifluoromethyl iodide from the reaction mixture in substantially pure form.

23. The process of claim 1, wherein the catalyst is present at 7.5 wt. %.

24. The process of claim 1, wherein the catalyst promoter is present at 1 wt. %.

25. The process of claim 1, wherein the catalyst promoter is present at 2 wt. %.

26. The process of claim 1, wherein the catalyst promoter is present at 5 wt. %.

27. A process for the preparation of a fluoroiodoalkane compound represented by the formula:

$CF_3(CF_2)_n$—I wherein n is 0 or 1;
the process comprising contacting:
   (i) a compound represented by the formula:

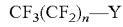

$CF_3(CF_2)_n$—Y wherein Y is selected from the group consisting of: H, Cl, and Br;
wherein n is 0 or 1;
   (ii) a source of iodine;
   (iii) an alkali metal salt catalyst selected from the group consisting of K, Rb and Cs, and
   (iv) a catalyst promoter in the range of from 0.01 to 50% by weight of the entire catalyst weight,
at a temperature for a length of time sufficient to produce the fluoroiodoalkane compound and
wherein the catalyst promoter comprises $Sm_2O_3$.

28. The process of claim 27, wherein the reaction is carried out in the presence of oxygen.

29. The process of claim 27, wherein the reaction is carried out in the absence of oxygen.

30. The process of claim 27, wherein the catalyst carrier is carbonaceous.

31. The process of claim 27, wherein the catalyst carrier is non-carbonaceous.

32. The process of claim 27, wherein the source of iodine is a compound selected from the group consisting of $I_2$, HI, ICl, $IF_5$, and any combination thereof.

33. The process of claim 27, wherein the source of iodine is $I_2$.

34. The process of claim 27, wherein the step of contacting is carried out at a temperature from about 300° C. to about 600° C.

35. The process of claim 27, wherein the step of contacting is carried out at a temperature from about 400° C. to about 550° C.

36. The process of claim 27, wherein the step of contacting is carried out at a pressure from about 0.1 atm to about 100 atm.

37. The process of claim 27, wherein the step of contacting is carried out at a pressure from about 0.5 atm to about 5 atm.

38. The process of claim 27, wherein the step of contacting is carried out for a length of time from about 0.01 seconds to about 300 hours.

39. The process of claim 27, wherein the step of contacting is carried out for a length of time from about 0.05 seconds to about 10 hours.

40. The process of claim 27, wherein the step of contacting is carried out for a length of time from about 1 second to about 10 minutes.

41. The process of claim 27, wherein the process is a batch process.

42. The process of claim 27, wherein the process is a continuous process.

43. The process of claim 27, wherein the contacting is carried out in a fixed-bed reactor.

44. The process of claim 27, wherein the contacting is carried out in a moving-bed reactor.

45. The process of claim 27, further comprising a diluent selected from the group consisting of a gas, a solvent, and a combination thereof.

46. The process of claim 27, wherein the diluent is a gas selected from the group consisting of nitrogen, helium, argon and any combination thereof.

47. The process of claim 27, wherein the diluent is a solvent of a liquid or gaseous fluorocarbon.

48. The process of claim 27, further comprising at least one step selected from the group consisting of the following:
   a) passing the trifluoromethyl iodide through a scrubber containing an aqueous alkali solution;
   b) passing the trifluoromethyl iodide through a scrubber containing a drying agent;
   c) cooling at a temperature below the boiling temperature of the trifluoromethyl iodide to condense; and
   d) isolating the trifluoromethyl iodide from the reaction mixture in substantially pure form.

49. The process of claim 27, wherein the catalyst is present at 7.5 wt. %.

50. The process of claim 27, wherein the catalyst promoter is present at 1 wt. %.

51. The process of claim 27, wherein the catalyst promoter is present at 2 wt. %.

52. The process of claim 27, wherein the catalyst promoter is present at 5 wt. %.

* * * * *